(12) United States Patent
Konno et al.

(10) Patent No.: US 7,015,700 B2
(45) Date of Patent: Mar. 21, 2006

(54) FLAW DETECTOR

(75) Inventors: Hidetoshi Konno, Tokyo (JP);
Yasuyuki Moriyama, Tokyo (JP);
Michio Sugata, Tokyo (JP)

(73) Assignee: Tetra Laval Holdings & Finance S.A., (CH)

( * ) Notice: Subject to any disclaimer, the term of this patent is extended or adjusted under 35 U.S.C. 154(b) by 322 days.

(21) Appl. No.: 10/432,908

(22) PCT Filed: Dec. 26, 2001

(86) PCT No.: PCT/JP01/11432

§ 371 (c)(1),
(2), (4) Date: May 29, 2003

(87) PCT Pub. No.: WO02/054053

PCT Pub. Date: Jul. 11, 2002

(65) Prior Publication Data

US 2004/0027133 A1 Feb. 12, 2004

(30) Foreign Application Priority Data

Dec. 27, 2000 (JP) .............................. 2000-399148

(51) Int. Cl.
*G01N 27/02* (2006.01)

(52) U.S. Cl. ..................................................... 324/444
(58) Field of Classification Search ........ 324/557–559, 324/444–450; 73/49.3; 82/1.11
See application file for complete search history.

(56) References Cited

U.S. PATENT DOCUMENTS

| 4,125,805 A | * | 11/1978 | Nagamatsu et al. | ........ 324/558 |
| 4,243,932 A | * | 1/1981 | Kakumoto et al. | ......... 324/557 |
| 4,291,600 A | * | 9/1981 | Kawaguchi et al. | ......... 82/1.11 |
| 5,760,295 A | * | 6/1998 | Yasumoto | ................... 73/49.3 |

* cited by examiner

*Primary Examiner*—Vincent Q. Nguyen
(74) *Attorney, Agent, or Firm*—Lorusso & Loud

(57) ABSTRACT

Flaw detection apparatus includes an electrode disposed in a region surrounded by a packaging material including a layer of an electrically-conductive material; a cutting member made of an electrically-conductive material and adapted to cut a predetermined portion of the packaging material; a variable detector, disposed between the electrode and the cutting member, for detecting an electrical variable; and flaw detection processor for reading the detected variable and for determining, on the basis of the detected variable, a flaw in the packaging material. In this case, the variable detector is disposed between the electrode and the cutting member.

3 Claims, 3 Drawing Sheets

FLAW DETECTOR

CROSS-REFERENCE TO RELATED APPLICATIONS

The present application is a 371 of PCT/JP01/11432 filed Dec. 27, 2000 and claims priority under 35 USC 365 of Japanese Application No. 2000-399148 filed Dec. 26, 2001.

TECHNICAL FIELD

The present invention relates to a flaw detection apparatus.

BACKGROUND ART

Conventionally, liquid foods such as milk and other beverages have been sold while accommodated within, for example, packaging containers formed from a packing material having a paper substrate. Examples of such packaging containers include polyhedral packaging containers and brick-shaped packaging containers each having a flat top wall. Of these packaging containers, packaging containers having a capacity which enables a purchaser to drink liquid food in a single serving are formed through a process of longitudinally sealing a web-shaped packaging material into a tubular shape, transversely sealing and cutting the tube-shaped packaging material at predetermined intervals to thereby form initial-shape containers, and processing the initial-shape containers to complete the packaging containers. Further, a discharge opening is formed in the top wall of each packaging container and is covered with a pull tab from the outer side and with an inner seal from the inner side, and the pull tab and the inner seal are welded together.

During fabrication of the above described packaging container, heat is applied to the packaging material, the pull tab, and the inner seal in order to seal the packaging material in the longitudinal and transverse directions and to weld the pull tab and the inner seal together. At that time, stress acts on resin layers which constitute the pull tab and the inner seal, respectively, possibly resulting in formation of flaws such as pinholes and cracks in the packaging material. If such a flaw is generated in, for example, the innermost resin layer of the packaging material, an aluminum foil layer, and the inner seal, the liquid food contained in the packaging container soaks into the paper substrate, and oozes from an end surface of the packaging material or from the interface between the container body of the packaging container and the pull tab.

In view of the forgoing, there has been provided a flaw detection apparatus which samples packaging containers at proper intervals; forms an opening in the top wall of each sampled packaging container; charges water into the packaging container; and immerses a portion of the water-charged packaging container into water stored in a vessel. Since an end surface of the aluminum foil layer is exposed to the outside of the packaging container, when electrodes are dipped in the water within the packaging container and the water within the vessel, respectively, electrical continuity is established between the two electrodes if a pinhole has formed in the packaging container to a depth reaching the aluminum foil layer.

However, since the conventional flaw detection apparatus requires the labor of charging water into each packaging container and partially immersing the packaging container in water stored in the vessel, the labor for flaw detection is cumbersome. Further, the flaw detection apparatus cannot inspect all packaging containers. In addition, since the flaw detection apparatus forms an opening in the top wall of packaging containers to be inspected, the inspected packaging containers are destroyed.

An object of the present invention is to solve the problems involved in the above described conventional flaw detection apparatus and to provide a flaw detection apparatus which can simplify the labor necessary for flaw detection, which can inspect all packaging containers, and which does not destroy the packaging container during inspection.

DISCLOSURE OF THE INVENTION

In order to achieve the above object, a flaw detection apparatus according to the present invention comprises an electrode disposed in a region surrounded by a packaging material including a layer of an electrically-conductive material; a cutting member made of an electrically-conductive material and adapted to cut a predetermined portion of the packaging material; variable detection means, disposed between the electrode and the cutting member, for detecting an electrical variable; and flaw detection processing means for reading the detected variable and for determining, on the basis of the detected variable, a flaw generated in the packaging material.

In this case, since inspection for detecting a flaw in the packaging container does not require charging water into each packaging container and partially immersing the packaging container in water contained in a vessel, the labor for flaw detection is simplified. Further, all packaging containers can be inspected. Moreover, since no opening is formed in the top wall of each of packaging containers to be inspected, the packaging containers are not destroyed during inspection.

The flaw detection apparatus of the present invention may further include a sealing apparatus for sealing the packaging material; and the predetermined portion of the packaging material is a seal formed by the sealing apparatus.

In the flaw detection apparatus of the present invention, the flaw detection processing means preferably reads the electrical variable at the time when the cutting member cuts the seal.

In using the flaw detection apparatus of the present invention liquid food may be charged into the region, and the electrode dipped in the liquid food.

DESCRIPTION OF THE PREFERRED EMBODIMENT

Figure 1:
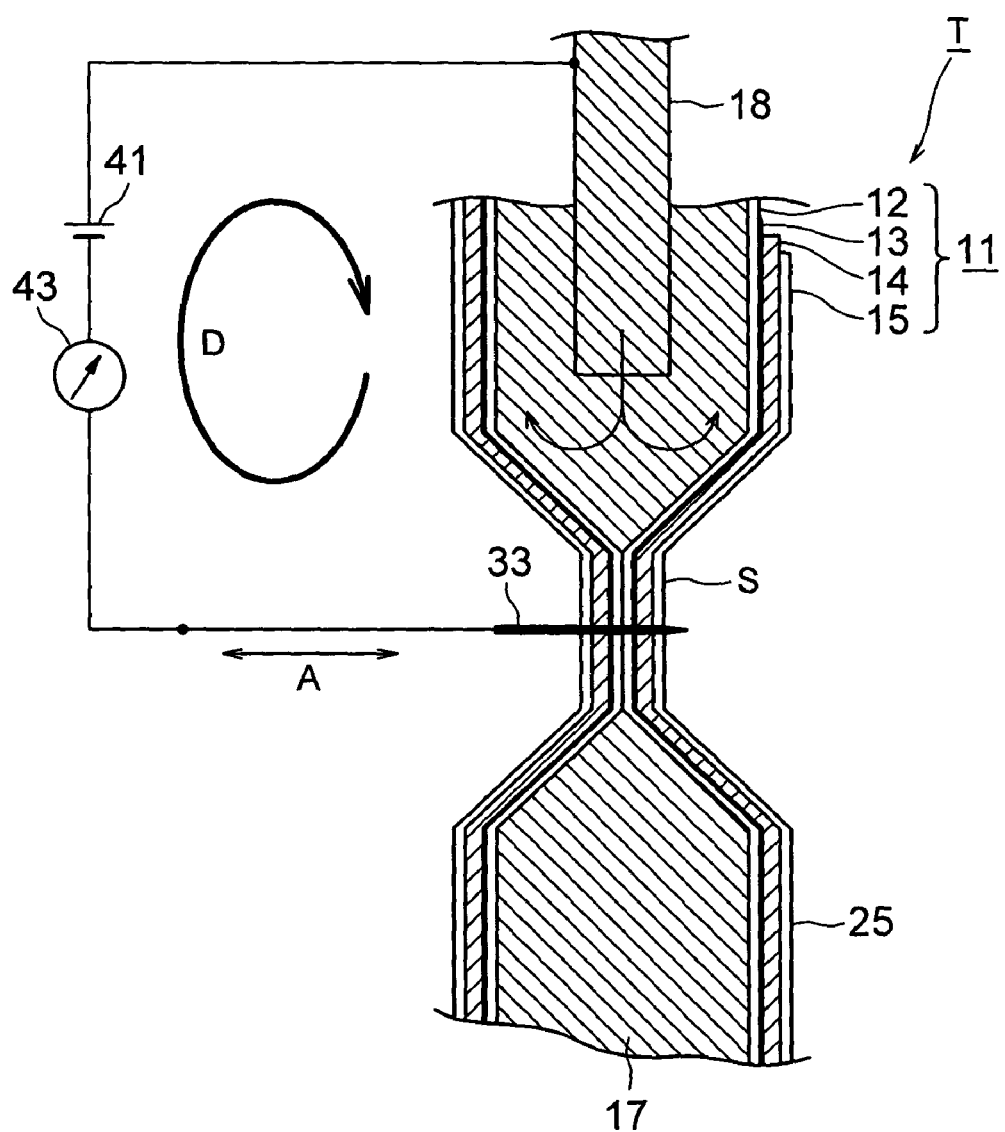
FIG. 1 is a schematic view of a flaw detection apparatus according to an embodiment of the present invention.

The embodiment of the present invention will next be described in detail with reference to the drawings.

In the drawings, reference numeral 11 denotes a packaging material formed from a flexible material; e.g., a laminate that includes a first resin layer 12 made of polyethylene or like resin, an electrically conductive aluminum foil layer 13, a paper substrate 14, and a second resin layer 15 made of polyethylene or like resin, which are arranged in this order from the inner side. When the packaging material 11 is unwound from a reel (unillustrated), the packaging material 11 assumes a web-like shape. Subsequently, the packaging material 11 is sealed longitudinally, while being transported, so as to form a longitudinal seal portion (unillustrated), whereby the packaging material 11 becomes a tubular packaging material; i.e., a tube T.

Figure 2:
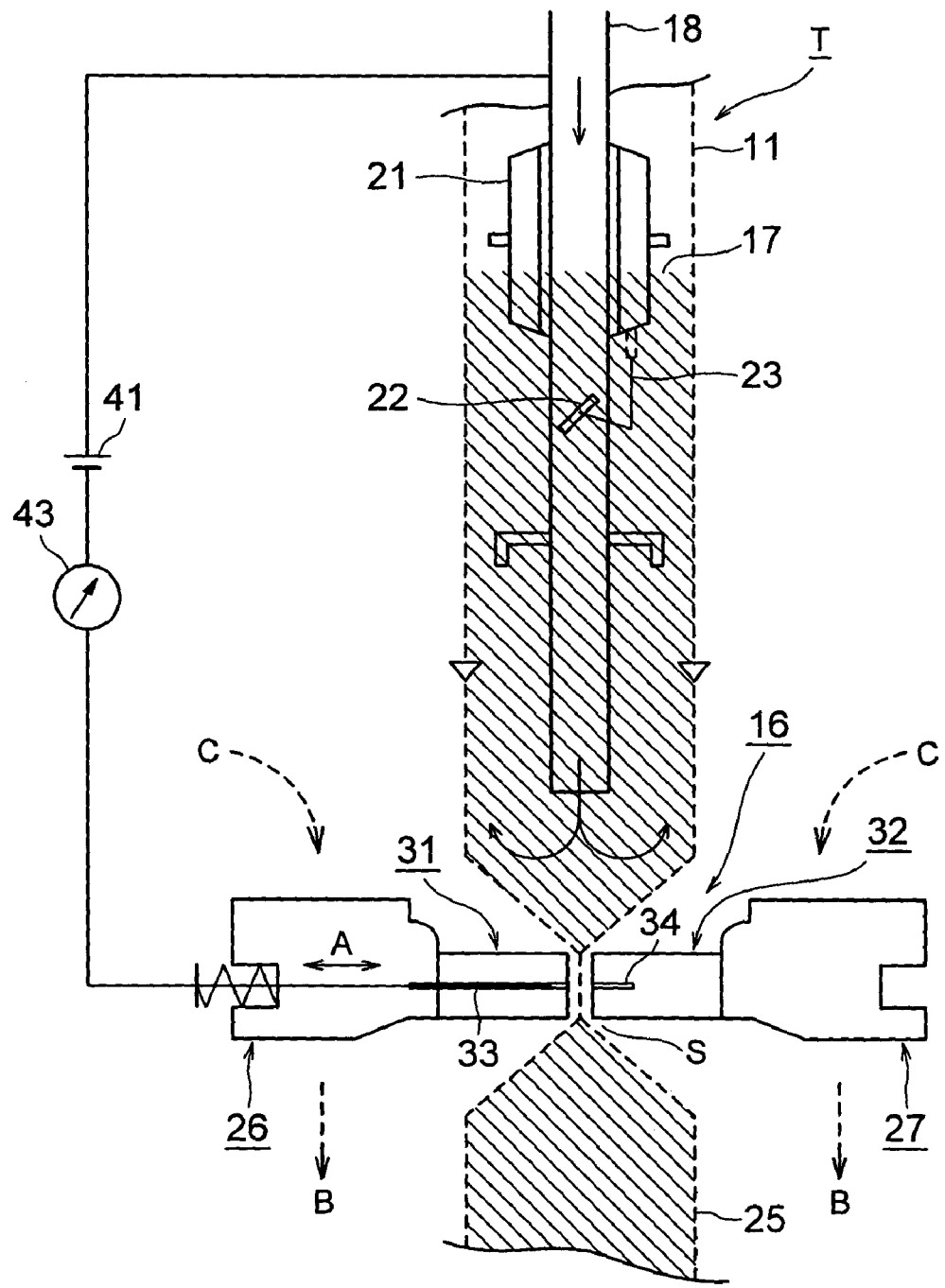
FIG. 2 is a schematic view of a main portion of a charging machine according to the embodiment of FIG. 1.

The tube T is continuously transported downward by means of a transfer apparatus (unillustrated) and is nipped by two seal-cut units 16 (only one seal-cut unit 16 is shown in FIG. 2) at predetermined intervals, whereby the tube T is sealed transversely and a belt-shaped lateral seal portion S is formed. Each of the seal-cut units 16 includes a cutting jaw 26 and a pressure jaw 27. A cutting bar 31 is disposed at the front end (the right-hand end in FIG. 2) of the cutting jaw 26. An inductor 32 serving as seal means is disposed at the front end (the left-hand end in FIG. 2) of the pressure jaw 27. By advancing both the cutting jaw 26 and the pressure jaw 27 (moving the cutting jaw 26 rightward in FIG. 2 and the pressure jaw 27 leftward in FIG. 2), the tube T is nipped from both sides, so that opposing portions of the packaging material 11 are pressed against each other, and opposing portions of the first resin layer 12 are welded. Thus, the tube T is sealed transversely.

A liquid food 17 is charged into the region surrounded by the packaging material 11; i.e., within the tube T, from above. For this charging, a charge pipe 18, which is formed of an electrically conductive material such as a metal and which serves an electrode, is inserted into the tube T. The charge pipe 18 extends downward and has an open lower end. The liquid food 17 is supplied from a liquid food supply source (unillustrated) to the charge pipe 18, so that the liquid food 17 is discharged from the lower end of the charge pipe 18 into the tube T in the direction of arrows B shown in FIG. 2. Thus, the lower end of the charge pipe 18 is dipped in the liquid food 17 and is in electrical contact with the liquid food 17. Although the charge pipe 18 is formed of a metal in the present embodiment, alternatively the charge pipe 18 may be formed of an electrically conductive resin.

In order to maintain the liquid food 17 at a constant level within the tube T, there are provided: a float 21; an open/close valve 22 disposed within the charge pipe 18 for movement between an open position and a closed position; and a link 23 which connects the float 21 and the open/close valve 22. As the level of the liquid food 17 rises, the float 21 moves upward, and the open/close valve 22 is closed by means of the link 23 so as to stop charging of the liquid food 17. When the level of the liquid food 17 falls, the float 21 moves downward, and the open/close valve 22 is opened by means of the link 23 so as to charge the liquid food 17.

After completion of charging of the liquid food 17 and formation of the lateral seal portion S, the lateral seal portion S is cut in order to obtain an initial-shape container 25 containing a predetermined amount of the liquid food 17.

Figure 3:
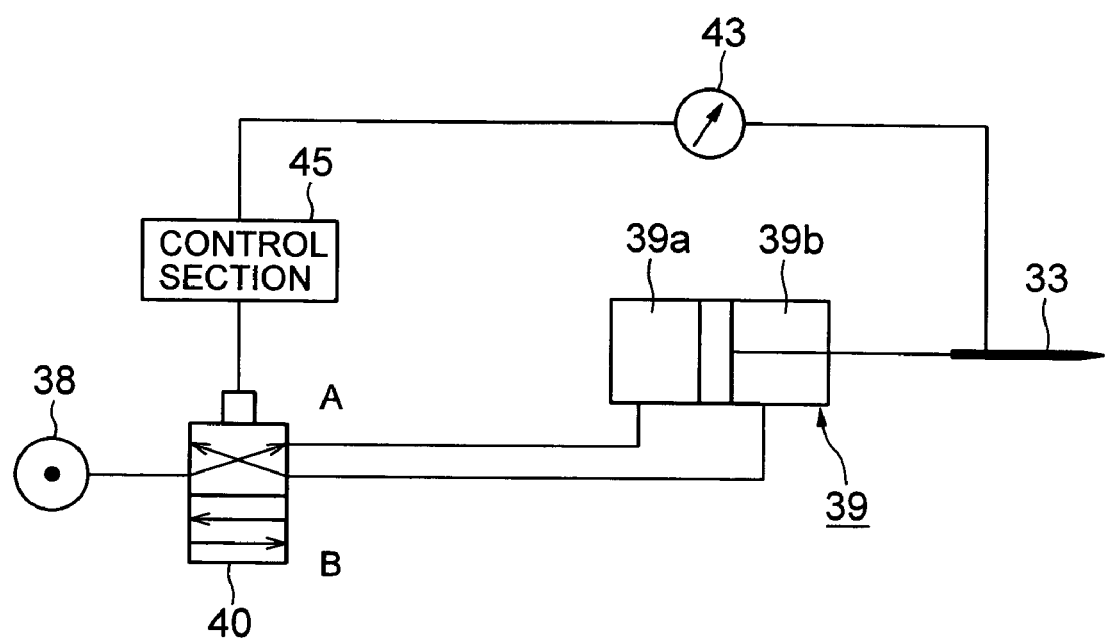
FIG. 3 is a block diagram of the flaw detection apparatus according to the embodiment of FIG. 1.

For such cutting operation, a horizontally extending flat cutter 33 is disposed at the center of the cutting bar 31 in such a manner that the cutter 33' can advance and retract (in the direction of arrow A). When the cutter 33 is advanced (moved rightward in FIG. 2), the cutter 33 cuts the tube T at a predetermined location (in the present embodiment, at the center of the lateral seal portion S) of the packaging material 11. Specifically, an air cylinder 39, serving as an actuator, is disposed at the rear end (the left-hand end in FIG. 3) of the cutter 33, and an operation medium such as compressed air is supplied from a compressed air source 38 via a changeover valve 40. Through supply and release of compressed air via the changeover valve 40, the cutter 33 can be advanced and retracted. The changeover valve 40 assumes position A or B in accordance with a changeover signal from a control section 45. At position A, the changeover valve 40 supplies compressed air from the compressed air source 38 to a chamber 39a of the air cylinder 39, and discharges compressed air from a chamber 39b of the air cylinder 39. At position B, the changeover valve 40 supplies compressed air from the compressed air source 38 to the chamber 39b of the air cylinder 39, and discharges compressed air from the chamber 39a of the air cylinder 39. A groove 34 is formed in the inductor 32 so as to accommodate a tip end of the cutter 33 when the cutter 33 is advanced.

In FIG. 2, the seal-cut unit 16 is shown located in a seal-cut start position, at which the cutting jaw 26 and the pressure jaw 27 are advanced. Subsequently, the seal-cut unit 16 is moved downward (in the direction of arrow B) while nipping the tube T, while the cutting bar 31 and the inductor 32 are strongly pressed against the tube T, and the inductor 32 heats the aluminum foil layer 13 by means of inductive heating. As a result, the opposed portions of the first resin layer 12 are welded to thereby seal the tube T transversely. Although in the present embodiment the tube T is sealed by use of the inductor 32 through inductive heating, the tube T may be sealed by use of a resistor which generates Joule heat.

Subsequently, the seal-cut unit 16 is moved further downward (in the direction of arrow B), while cutting processing means (unillustrated) of the control section 45 causes the changeover valve 40 to assume position A in order to advance the cutter 33 to thereby cut the lateral seal portion S at the-center thereof. Thus, a rectangular initial-shape container 25 is separated from the tube T. The seal-cut unit 16 then reaches a seal-cut end position.

Subsequently, the cutting processing means causes the changeover valve 40 to assume position B in order to retract the cutter 33 and simultaneously retract the cutting jaw 26 and the pressure jaw 27 (move the cutting jaw 26 leftward in FIG. 2 and the pressure jaw 27 rightward in FIG. 2). Subsequently, the seal-cut unit 16 is moved upward and then moved along the direction or arrow C to the seal-cut start position.

The initial-shape container 25, which has been formed in the above-described manner, is transported to a forming machine (unillustrated), and is formed into a predetermined shape by the forming machine, whereby a packaging container is obtained.

During fabrication of the above-described packaging container, because heat is applied to the packaging material 11 in order to seal the packaging material 11 in the longitudinal and transverse directions, stress acts on the first resin layer 12, the second resin layer 15, and the aluminum foil layer 13, which constitute the packaging material 11, possibly resulting in formation of flaws such as pinholes and cracks in the packaging material 11. If such a flaw is formed in the first resin layer 12 or the aluminum foil layer 13, the liquid food 17 contained in the packaging container soaks into the paper substrate 14, and oozes from an end surface of the packaging material 11.

In view of the foregoing, the cutter 33 is formed of an electrically conductive material such as a metal; and the charge pipe 18 and the cutter 33 are in electrical contact via a power source 41 and a current sensor 43, which serves as variable detection means, in order to detect any flaw formed in the packaging material 11. Again, the electrically conductive material may be an electrically conductive resin.

Current is detected by the current sensor 43 as an electrical variable, and a sensor output representing the detected current is fed to the control section 45. At the time the cutting processing means causes the changeover valve 40 to assume position A in order to cut the lateral seal portion S by means of the cutter 33, the flaw detection processing means of the control section 45 reads the sensor output fed from the current sensor 43, and detects any flaw in the packaging material 11 on the basis of the sensor output.

Thus, electrical continuity is established between the cutter 33 and the aluminum foil layer 13 when the advancing cutter 33 is cutting the lateral seal portion S at the center thereof. Therefore, when a flaw such as pinhole or crack is formed in at least the first resin layer 12, electrical continuity is established between the liquid food 17 and the aluminum foil layer 13 at the location where the flaw has formed, so that a closed loop is formed by the cutter 33, the current sensor 43, the power source 41, the charge pipe 18, the liquid food 17, and the aluminum foil layer 13, and current flows through the closed loop in the direction of arrow D in FIG. 1, which current is detected by the current sensor 43.

As described above, since the detection of a flaw in the packaging material does not require charging water into each packaging container and partially immersing the packaging container in water contained in a vessel, the labor for flaw detection is simplified. Further, all packaging containers can be inspected. Moreover, since an opening is not formed in the top wall of each of the packaging containers to be inspected, the packaging containers are not destroyed during inspection.

In the present embodiment, the current sensor 43 is used as the variable detection means in order to detect current serving as the electrical variable. However, as an alternative, a voltage sensor may be used as the variable detection means in order to detect voltage as the electrical variable.

In the present embodiment, the aluminum foil layer 13 is formed within the packaging material 11 and electrical continuity between the liquid food 17 and the aluminum foil layer 13 at the location of a flaw is detected. However, instead of the aluminum foil layer 13, a layer of an electrically conductive material such as a metal (e.g., steel) or an electrically conductive resin may be formed within the packaging material 11, in which case electrical continuity between the liquid food 17 and the electrically conductive material layer at the location of a flaw is detected.

In the present embodiment, the charge pipe 18 serves as an electrode. However, an electrode provided in the tube T separately from the charge pipe 18 may be dipped in the liquid food 17, in which case electrical continuity between the electrode and the cutter 33 via the power source 41 and the current sensor 43 is established in order to detect a flaw formed in the packaging material 11.

In the present embodiment, sealing and cutting are performed simultaneously by the inductor 32 and the cutter 33, respectively. However, cutting may be performed after completion of sealing.

The present invention is not limited to the embodiments described above. Numerous modifications and variations of the present invention are possible in light of the spirit of the present invention, and they are not excluded from the scope of the present invention.

The invention claimed is:

1. A flaw detection apparatus comprising:
   (a) an electrode disposed dipped into liquid food charged into a region surrounded by a packaging material including a layer of an electrically-conductive material;
   (b) a cutting member made of an electrically-conductive material and adapted to cut a predetermined portion of the packaging material;
   (c) variable detection means, disposed between the electrode and the cutting member, for detecting an electrical variable; and
   (d) flaw detection processing means for reading the detected electrical variable and for detecting, on the basis of the detected electrical variable, a flaw generated in the packaging material.

2. A flaw detection apparatus according to claim 1, wherein
   (a) the flaw detection apparatus further comprises a seal apparatus for sealing the packaging material; and
   (b) the predetermined portion of the packaging material is a seal portion formed by the seal apparatus.

3. A flaw detection apparatus according to claim 1, wherein the flaw detection processing means reads the detected electrical variable at a time when the cutting member cuts a seal portion.

* * * * *